(12) United States Patent
Stroppolo et al.

(10) Patent No.: US 8,574,552 B2
(45) Date of Patent: Nov. 5, 2013

(54) SOLID DOSAGE FORMULATIONS OF NARCOTIC DRUGS HAVING IMPROVED BUCCAL ADSORPTION

(75) Inventors: Federico Stroppolo, Mezzovico (CH); Shahbaz Ardalan, Maroggia (CH)

(73) Assignee: Alpex Pharma S.A., Mezzovico (CH)

( * ) Notice: Subject to any disclaimer, the term of this patent is extended or adjusted under 35 U.S.C. 154(b) by 1167 days.

(21) Appl. No.: 11/490,500

(22) Filed: Jul. 21, 2006

(65) Prior Publication Data

US 2007/0020187 A1    Jan. 25, 2007

Related U.S. Application Data

(63) Continuation-in-part of application No. 11/186,925, filed on Jul. 22, 2005, now abandoned.

(51) Int. Cl.
*A61K 9/44* (2006.01)
*A61K 31/485* (2006.01)
*A61K 31/445* (2006.01)
*A61K 31/425* (2006.01)

(52) U.S. Cl.
USPC .......... 424/10.2; 514/317; 514/565; 514/553; 514/561; 514/282

(58) Field of Classification Search
None
See application file for complete search history.

(56) References Cited

U.S. PATENT DOCUMENTS

| | | | |
|---|---|---|---|
| 5,464,632 A | 11/1995 | Cousin et al. | |
| 5,501,861 A | 3/1996 | Makino et al. | |
| 5,576,014 A | 11/1996 | Mizumoto et al. | |
| 5,624,677 A | 4/1997 | El-Rashidy et al. | |
| 5,720,974 A | 2/1998 | Makino et al. | |
| 5,785,989 A | 7/1998 | Stanley et al. | |
| 5,869,098 A | 2/1999 | Misra et al. | |
| 5,888,534 A | 3/1999 | El-Rashidy et al. | |
| 5,958,453 A | 9/1999 | Ohno et al. | |
| 6,024,981 A | 2/2000 | Khankari et al. | |
| 6,149,938 A | 11/2000 | Bonadeo et al. | |
| 6,200,604 B1 * | 3/2001 | Pather et al. | 424/466 |
| 6,210,699 B1 | 4/2001 | Acharya et al. | |
| 6,221,392 B1 | 4/2001 | Khankari et al. | |
| 6,264,981 B1 | 7/2001 | Zhang et al. | |
| 6,316,027 B1 | 11/2001 | Johnson et al. | |
| 6,350,470 B1 | 2/2002 | Pather et al. | |
| 6,471,991 B2 | 10/2002 | Robinson et al. | |
| 6,509,028 B2 | 1/2003 | Williams et al. | |
| 6,680,071 B1 | 1/2004 | Johnson et al. | |
| 6,733,781 B2 | 5/2004 | Abu-Izza et al. | |
| 6,974,590 B2 | 12/2005 | Pather et al. | |
| 2001/0051186 A1 | 12/2001 | Acharya et al. | |
| 2002/0013331 A1 | 1/2002 | Williams et al. | |
| 2002/0192288 A1 | 12/2002 | Williams et al. | |
| 2003/0082107 A1 * | 5/2003 | Dugger, III | 424/43 |
| 2003/0104041 A1 * | 6/2003 | Hsu et al. | 424/449 |
| 2003/0215502 A1 | 11/2003 | Pruss et al. | |
| 2004/0253307 A1 * | 12/2004 | Hague et al. | 424/464 |
| 2005/0013857 A1 | 1/2005 | Fu et al. | |

FOREIGN PATENT DOCUMENTS

| | | |
|---|---|---|
| JP | 10-095738 | 4/1998 |
| JP | 2000-281589 | 10/2000 |
| WO | 2004-089336 A2 | 10/2004 |

OTHER PUBLICATIONS

Senal and Hincal, Permeation enhancement via buccal route: possibilities and limitations, Journal of Controlled Release, 72 (2001) 133-144.*
Rossi et al, Drug discovery today: technologies, vol. 2, No. 1, 2005, pp. 59-65.*
Zhang et al, Clinical pharmacokinetics, 2002: 41 (9): pp. 661-680.*
Office action and search report dated Mar. 29, 2012 from Japanese Patent Office for application serial No. 2008-521904, 3 pages.
Streisand, J. B., et al., "Buccal absorption of fentanyl is pH-dependent in dogs," Anesthesiology 1995, 82 (3):759-764.
Letter of Examination Report dated Dec. 23, 2011, and a search report (English translation) for Taiwanese application No. 095126670, 3 pages.

* cited by examiner

*Primary Examiner* — Bong-Sook Baek
*Assistant Examiner* — Taina D Matos Negron
(74) *Attorney, Agent, or Firm* — Rothwell, Figg, Ernst & Manbeck, P.C.

(57) ABSTRACT

Disclosed is a pharmaceutical composition in the form of a tablet suitable for dissolution in the buccal cavity, said composition comprising
  i) an effective amount of a narcotic active ingredient, and
  ii) a pharmaceutically acceptable amine having a pK of about 8 or greater,
wherein the molar ratio of amine:active ingredient is at least about 5:1.

2 Claims, No Drawings

SOLID DOSAGE FORMULATIONS OF NARCOTIC DRUGS HAVING IMPROVED BUCCAL ADSORPTION

CROSS REFERENCE TO RELATED APPLICATIONS

This application is a continuation-in-part of application Ser. No. 11/186,925 filed Jul. 22, 2005.

STATEMENT REGARDING FEDERALLY SPONSORED RESEARCH OR DEVELOPMENT

Not applicable.

BACKGROUND OF THE INVENTION

Buccal formulations are more and more popular for drug administrations. They exhibit in fact several advantages in comparison with other solid dosage forms; in particular, buccal formulations dissolve in the oral cavity without requiring water for ingestion, allowing the buccal adsorption of drugs coming into contact with the oral mucosa in dissolved form. Sometimes, buccal administration does not unfortunately always allow to obtain a fast onset of action of the drug, as the result of difficulties of the drug to cross the skin barrier of mucosa and to penetrate into the blood stream.

DESCRIPTION OF THE INVENTION

The present invention concerns solid dosage formulations of narcotic drugs having improved buccal adsorption.

The formulations of the invention are characterized by the introduction in a buccal formulation of a pharmaceutically acceptable soluble organic compound having a primary, secondary or tertiary amine group, having a pK of about 8 or greater. Preferably, the in vivo disintegration time of tablets occurs in a time between about 5 and about 25 minutes.

Surprisingly, it has been found that adding a non-toxic or pharmaceutically acceptable amine to a buccal formulation, the penetration capacity of drugs is significantly improved, allowing to reach a higher and earlier blood concentration of the active ingredient in comparison with formulations without an amine as described herein.

Non-toxic amines having a pK of about 8 or greater which improve the bioavailability according to the invention belong to the following categories:

basic amino acids, such as Arginine, Lysine, Histidine, and Ornithine;
tertiary amines, such as Triethanolamine, and Thromethamine;
aminosulfonic acids, such as Taurine;
mercapramines such as Cysteamine;
quaternary ammonium salts, such as Betaine;
heterocyclic amines, such as Pyrrolidine; and
Guanidines.

Arginine is a preferred non-toxic amine. The formulations of the invention may include a mixture of two or more of said amines. Preferably, the amine is not polyvinylpyrrolidone.

Examples of active components that may be advantageously formulated in solid dosage form according to the invention include:

Alfentanil, Buprenorphine, Butorphanol, Codeine, Diphenoxylate, Fentanyl, Heroin, Hydrocodone, Hydromorphone, Oxymorphone, Levophanol, Levallorphan, Loperamide, Meperidine, Morphine, Nalbuphine, Nalmefene, Nalorphine, Naloxone, Naltrexone, Remifentanyl, Sufentanyl and derivatives, salts and analogues thereof. Fentanyl is preferred. The invention further includes the use of pharmaceutically acceptable forms of the active ingredient, such as salts, hydrates, etc., for example, Fentanyl citrate.

Preferably, the amount of amine in respect to the active ingredient (molar ratio active ingredient:amine) ranges from about 5:1 to about 1000:1, preferably from about 10:1 to about 500:1, and most preferably from about 20:1 to about 250:1.

Preferably, the disintegration time in vivo ranges between about 2 and about 50 minutes, more preferably between about 5 and about 25 minutes.

It will be understood that the present formulations may additionally contain ingredients typically found in tablets intended for buccal administration, such as one or more of diluents, binders, lubricants, glidants, disintegrants, coloring agents, flavouring agents, etc. The tablets may be made by conventional techniques, including wet, dry or fluid-bed granulation methods, or direct compression. Preferably, the tablets are not lyophilized.

The invention is illustrated by the following non-limiting Examples:

EXAMPLE #1

Example #1A

Preparation of an Oral Dispersible Tablet Containing Amine (Arginine)

Oral dispersible tablets containing 200 mcg of Fentanyl were obtained as follows:

A) 1.05 g of Fentanyl citrate and 50 g of PEG 6000 were dissolved into 90 g of purified water.

B) 335.62 g of Sorbitol, 516.67 g of Mannitol, 26.67 g of aspartame and 10 g of Citric acid, were granulated together with a water solution containing PEG and Fentanyl citrate.

C) At the end of granulation and drying, 43.33 g of arginine free base and 16.67 g of magnesium stearate were added.

D) The product was blended until homogeneity and compressed in toroidal tablets having a diameter of 10 mm and weighing 300 mg each and having hardness of about 70 Newton.

Comparative Example #1B

Preparation of an Oral Dispersable Tablet Without Amine

Oral dispersible tablets containing 400 mcg of Fentanyl have been obtained as follows:

E) 2.1 g of Fentanyl citrate and 50 g of PEG 6000 were dissolved into 90 g of purified water.

F) 455.62 g of Sorbitol, 455.62 g of Mannitol, 26.67 g of aspartame and 10 g of Citric acid, were granulated together with a water solution containing PEG and Fentanyl citrate.

G) The product was blended until homogeneity and compressed in toroidal tablets having a diameter of 10 mm and weighing 300 mg each having hardness of tablets of 30 Newton.

Example #2

A pharmacokinetic study was carried out on 6 fasting healthy volunteers treated with a buccal formulation prepared in accordance with example #1A containing 200 mcg of Fentanyl. The results were compared with a pharmacokinetic study carried out on 6 healthy volunteers treated with a buccal formulation prepared in accordance with example #1B containing 400 mcg of Fentanyl.

The results are reported in the following Table 1:

|  | Fentanyl strength per dosage | Disintegration Time in vivo | T max | C max | AUC |
| --- | --- | --- | --- | --- | --- |
| Example #1A | 200 mcg | 15 minutes | 48 minutes | 496 pg/ml | 2430 h * (pg/ml) |
| Example #1B | 400 mcg | 5 minutes | 35 minutes | 491 pg/ml | 3331 h * (pg/ml) |

Despite the dose of Fentanyl administered in the tablets described in example #1A (200 mcg) being 50% of the dose described in example #1B (400 mcg), the pharmacokinetic parameters are similar, demonstrating a dramatic improvement of the Fentanyl bioavailability for the formulation of the invention.

Example #3

A pharmacokinetic study was carried out on 6 fasting healthy volunteers treated with a buccal formulation prepared in accordance with example #1A containing 200 mcg of Fentanyl. The results were compared with a pharmacokinetic study carried out on 6 healthy volunteers treated with a buccal formulation commercially available (Actiq-commercialized by Cephalon, Inc., Salt Lake City, Utah 84116 USA) containing 200 mcg of Fentanyl.

The results are reported in the following Table 2:

|  | Fentanyl strength per dosage | Disintegration Time in vivo | T max | C max | AUC |
| --- | --- | --- | --- | --- | --- |
| Example #1A | 200 mcg | 15 minutes | 48 minutes | 496 pg/ml | 2430 h * (pg/ml) |
| Actiq | 200 mcg | 15 minutes | 3.25 hours | 237 pg/ml | 1607 h * (pg/ml) |

Despite the dose of Fentanyl administered in the tablets described in example #1A (200 mcg) being equal to the dose of Actiq (200 mcg), the pharmacokinetic parameters are much higher, demonstrating a dramatic improvement of the Fentanyl bioavailability for the formulation of the invention.

The invention claimed is:
1. A composition in the form of a tablet suitable for dissolution in the buccal cavity which comprises:
   about 0.1 weight % fentanyl citrate;
   about 4.3 weight % arginine;
   about 5.0 weight % PEG 6000;
   about 33.6 weight % sorbitol;
   about 51.7 weight % mannitol;
   about 2.7 weight % aspartame;
   about 1.0 weight % citric acid; and
   about 1.7 weight % magnesium stearate.
2. A method of administration of a narcotic to a mammal across the oral mucosa thereof, said method comprising orally administering to said mammal a pharmaceutical composition in the form of a tablet suitable for dissolution in the buccal cavity, said composition comprising:
   about 0.1 weight % fentanyl citrate;
   about 4.3 weight % arginine;
   about 5.0 weight % PEG 6000;
   about 33.6 weight % sorbitol;
   about 51.7 weight % mannitol;
   about 2.7 weight % aspartame;
   about 1.0 weight % citric acid; and
   about 1.7 weight % magnesium stearate.

* * * * *